United States Patent
Latimer et al.

(10) Patent No.: US 9,724,250 B2
(45) Date of Patent: Aug. 8, 2017

(54) UNITARY FLUID INTAKE SYSTEM FOR ABSORBENT PRODUCTS AND METHODS OF MAKING SAME

(71) Applicant: Kimberly-Clark Worldwide, Inc., Neenah, WI (US)

(72) Inventors: Margaret G. Latimer, Alpharetta, GA (US); John H. Conrad, Alpharetta, GA (US); Andrea S. Clewley, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 649 days.

(21) Appl. No.: 14/088,079

(22) Filed: Nov. 22, 2013

(65) Prior Publication Data

US 2015/0148764 A1 May 28, 2015

Related U.S. Application Data

(60) Provisional application No. 61/732,030, filed on Nov. 30, 2012.

(51) Int. Cl.
| | |
|---|---|
| *A61F 13/538* | (2006.01) |
| *A61F 13/15* | (2006.01) |
| *B32B 37/20* | (2006.01) |
| *A61F 13/534* | (2006.01) |
| *A61F 13/53* | (2006.01) |
| *B32B 37/00* | (2006.01) |

(52) U.S. Cl.
CPC ...... *A61F 13/538* (2013.01); *A61F 13/15699* (2013.01); *A61F 13/534* (2013.01); *B32B 37/203* (2013.01); *A61F 2013/530715* (2013.01); *B32B 2037/0092* (2013.01); *B32B 2305/20* (2013.01); *B32B 2555/02* (2013.01)

(58) Field of Classification Search
CPC .............. A61F 13/538; A61F 13/15699; A61F 2013/530715; B32B 37/14
See application file for complete search history.

(56) References Cited

U.S. PATENT DOCUMENTS

| | | | | |
|---|---|---|---|---|
| 5,350,370 A | * | 9/1994 | Jackson | A61F 13/53 604/358 |
| 5,599,335 A | * | 2/1997 | Goldman | A61L 15/42 604/368 |
| 5,879,343 A | * | 3/1999 | Dodge, II | A61F 13/15203 428/212 |
| 5,916,507 A | | 6/1999 | Dabi et al. | |
| 6,060,638 A | * | 5/2000 | Paul | A61F 13/15203 604/367 |

(Continued)

FOREIGN PATENT DOCUMENTS

| | | |
|---|---|---|
| EP | 0 539 703 A1 | 5/1993 |
| EP | 1 726 700 B1 | 2/2013 |

(Continued)

*Primary Examiner* — Jeremy R Pierce

(57) ABSTRACT

A unitary fabric structure for use within a personal care absorbent article includes a composite of at least two functional components for fluid intake. The two functional components include a fibrous, liner functional component and at least one fibrous, surge functional component. The functional components are positioned immediately adjacent one another within the composite and held together directly to one another.

13 Claims, 4 Drawing Sheets

(56) References Cited

U.S. PATENT DOCUMENTS

| | | | |
|---|---|---|---|
| 6,420,626 B1 | 7/2002 | Erspamer et al. | |
| 6,423,884 B1 | 7/2002 | Oehmen | |
| 6,613,028 B1 | 9/2003 | Daley et al. | |
| 2002/0026166 A1 | 2/2002 | Graef et al. | |
| 2003/0124927 A1* | 7/2003 | Waldroup | A61F 13/51104 442/50 |
| 2003/0130634 A1* | 7/2003 | Fenwick | A61F 13/5376 604/367 |
| 2004/0102752 A1* | 5/2004 | Chen | A61F 13/4751 604/378 |
| 2004/0235380 A1* | 11/2004 | Kapik | B32B 5/26 442/382 |
| 2005/0049566 A1 | 3/2005 | Vukos et al. | |
| 2007/0287348 A1* | 12/2007 | Autran | A61F 13/51464 442/327 |
| 2010/0167029 A1* | 7/2010 | Luo | B32B 5/26 442/340 |
| 2010/0206803 A1* | 8/2010 | Ward | B01D 39/1623 210/491 |
| 2010/0305536 A1* | 12/2010 | Fernkvist | A61F 13/15 604/372 |
| 2010/0310810 A1* | 12/2010 | Bond | A61F 13/511 428/74 |
| 2013/0221559 A1 | 8/2013 | Schafer et al. | |
| 2014/0050894 A1* | 2/2014 | Wahlquist | B32B 37/0084 442/335 |

FOREIGN PATENT DOCUMENTS

| | | |
|---|---|---|
| GB | 1 275 572 A | 5/1972 |
| WO | WO 97/13909 A2 | 4/1997 |
| WO | WO 99/63925 A1 | 12/1999 |
| WO | WO 01/72251 A1 | 10/2001 |
| WO | WO 2009/105000 A1 | 8/2009 |

\* cited by examiner

UNITARY FLUID INTAKE SYSTEM FOR ABSORBENT PRODUCTS AND METHODS OF MAKING SAME

PRIORITY APPLICATION

This application claims priority from U.S. provisional Patent Application Ser. No. 61/732,030 filed on Nov. 30, 2012, the entire contents of which are incorporated herein by reference.

FIELD OF INVENTION

The present invention pertains to fluid intake layers for personal care absorbent articles. In particular, the present invention pertains to fabrics of unitary construction for placement in personal care absorbent articles such as in baby and child care diapers, adult care incontinence articles, and feminine care hygiene articles, in which the unitary fabric structure performs multiple functions within the personal care absorbent article.

BACKGROUND

Disposable personal care absorbent articles are traditionally manufactured from a variety of fabrics, often nonwoven materials, that are delivered to manufacturing facilities on rolls for conversion into product. Many of these fabrics are the fluid intake materials of the articles. For the purposes of this application, the term "fluid intake" shall refer to those layers in an absorbent article through which fluid passes after being excreted from a user, as it travels to the primary fluid retention materials (sometimes referred to as the absorbent core) of the absorbent article. The term "fluid intake" does not encompass the primary fluid retention materials (such as for example superabsorbent materials and substantially cellulosic layers). A variety of fluid intake fabrics are often included in personal care product structures because they each offer particular functional benefits to the overall product. For example, some fluid intake materials may be more suitable as topsheet or liner layers that provide initial contact with the skin of a user, while others may better serve as fluid transfer or surge layers within the interior of a layered product. The term "surge layer" is so called because it assists in the control of surges of fluids, such as urine or menses, delivered by the wearer of the absorbent article that might result in leakage, if not for the surge layer. Still further, some materials may be best suited as absorbent core-encasing layers (or core wrap materials), allowing fluid to pass through into the fluid retaining absorbent core, but preventing components from within the absorbent core layer from leaking out of the product.

As a result of the wide variety of fabrics used for these disparate purposes, problems have been encountered in bringing these diverse fabrics together on a production line. Some of these functionally diverse fabrics are derived from relatively slow and inefficient manufacturing processes. Other materials are produced from extremely small diameter polymeric fibrous webs so as to trap particulates, and present manufacturing and cost challenges. Still other fabrics are produced at relatively higher basis weights than would normally be needed for adequate functionality, in order to allow for the high speed of unwinding and handling during conversion into product. For example, materials of a certain basis weight that could be satisfactory for use within a product, may be too delicate to withstand processing steps.

As a result of such material conversion needs, product conversion processes are often overloaded with the integration of specialized material layers, some of which overcompensate to accommodate the rigors of high-speed, multi-step manufacturing systems. As an example, fabric properties, such as thickness and density may change once wound on a storage roll. In order to provide for a desired final thickness and density in a converted product, a fabric layer may be manufactured at a certain pre-conversion specification, taking into account the changes which will eventually occur to the fabric once wound on, and unwound from a storage roll, and exposed to further processing. A need therefore exists for efficiently produced fluid intake materials which can handle the rigors of a product converting process.

The lamination of separately produced fluid intake layers also leads to inter-layer connectivity issues. For example, spatial gaps may exist between layers, thereby impacting fluid movement as it travels to a core layer. Adhesive (typically hydrophobic) between separately produced fluid intake layers may also impact fluid flow and result in a stiffer product. Such obstacles to fluid flow frequently hamper the rapid transition of fluid from one layer to the next. Therefore, a continuing need exists for absorbent articles with fewer fabric layers, and with fabric layers having more efficiently designed features/properties including a reduced mass, tighter connectivity, and lack of reliance on separate adhesive layers for bonding. Such efficiency would result in cost savings as well. Absorbent core layers in personal care absorbent articles often include small particles, such as superabsorbent polymer (SAP) particles, to enhance absorbent capacity of the articles. Such core layers are often enveloped by separate core wraps of cellulosic tissue or polymeric nonwoven materials. Such nonwoven materials often include small diameter fibers (meltblown fibers) so as to prevent the migration of the small SAP particles out of the articles. Attempts have been made to design core layer structures with modified wrapping. However, such wrapping often results in additional mass in the products, additional adhesive layers, and subsequently additional production costs. A need therefore exists for core wrap functionality in a product, with reduced mass and adhesive costs.

Attempts have been made to produce unitary absorbent fabrics that combine the features of what has been traditionally employed in multiple layers of absorbent material. Such unitary fabrics have resulted in only modest improvements in fluid handling behavior with thicknesses and fabric weights equal to or greater than the combined weight of the original absorbent layers traditionally used in such absorbent products. Most often, such unitary absorbent fabrics have resulted in less desired functionality than what would have been available through separate individual layers.

Obtaining additional functional performance often necessitates additional fabric layers or basis weights. Such additional layers and basis weight would typically add further cost and manufacturing challenges to converting systems. Without fabric mass reduction or added functional benefits, the development of unitary structures would not justify such conversion inefficiencies. A need therefore exists for such reduced mass fabrics that continue to provide the same or better functional expectations as previously utilized multi-layered fabrics, but at lower costs. Further, a need exists for such fabrics that could provide for multiple functionality, and which could be produced by simplified manufacturing systems. A need also exists for manufacturing processes that would reduce the amount of material integration steps needed to produce a personal care absorbent article.

SUMMARY OF THE INVENTION

In one embodiment of the invention a unitary fabric structure for use within a personal care absorbent article includes a composite of at least two functional components for fluid intake, wherein the two functional components include a fibrous, liner functional component and at least one fibrous, surge functional component. The functional components are positioned immediately adjacent one another within the composite and held together directly in facing contact with one another. In a second embodiment of the invention, the composite includes at least three functional components including a liner functional component and at least two surge functional components. In still a further alternative embodiment, the composite includes at least three functional components including a liner functional component, a surge functional component and a core wrap functional component. In another alternative embodiment, the unitary fabric structure includes a fibrous, liner functional component that is comprised of hydrophilic fibers demonstrating an advancing contact angle of between about 75 and 80° and comprised of between about 10 and 8 micron diameter ($\mu$), alternatively between about 12 and 18$\mu$, alternatively, between about 15 and 18$\mu$ fibers. In yet another alternative embodiment, the unitary fabric structure includes a fibrous, liner functional component including no more than 2 gsm of 6$\mu$ fibers or smaller dusting of fibers. In yet another alternative embodiment, the unitary fabric structure includes a fibrous, liner functional component having a basis weight of about 6 gsm. In still another alternative embodiment, a unitary fabric structure includes a fibrous, liner functional component having between about 4 and 6 gsm relatively larger fibers of a size greater than 10$\mu$, and between about 0 and 2 gsm relatively smaller fibers of a size less than 10$\mu$. In still another alternative embodiment, the unitary fabric structure includes a fibrous, liner functional component having a basis weight of about 6 gsm comprised substantially of relatively larger fibers of a size greater than 10$\mu$. In another alternative embodiment of the invention, the unitary fabric structure includes a fibrous, surge component including a mixture of relatively large diameter wettable fibers having a size of between about 25 and 40$\mu$, and relatively small diameter wettable fibers having a size of between about 8 and 18$\mu$, and the fibers demonstrate an advancing contact angle of between about 40 and 60°. In still another alternative embodiment of the invention, the unitary fabric structure surge component includes a mixture of fibers including fibers demonstrating either crimp, texture, curl, bends or combination thereof, such that the fibrous, surge component demonstrates a density of between about 0.03 and 0.05 g/cc. In another alternative embodiment of the invention, the fibrous, surge component demonstrates a basis weight of about 70-75 gsm. In still another alternative embodiment, the fibrous, surge component demonstrates a basis weight of about 72 gsm. In yet another alternative embodiment of the invention, the functional components are comprised of fiber compositions selected from the group consisting of polyester, polyamide, permanently wettable hydrophilic polyolefins, polylactic acid, homopolymers, bicomponent, or biconstituent fibers containing such polymers.

In still yet another alternative embodiment of the invention, the unitary fabric structure components include at least one fibrous material selected from the group consisting of meltblown fibers, spunbond fibers, staple fibers and coform materials. In another alternative embodiment of the invention, the unitary fabric structure has no component including greater than 30 percent wood pulp-based fibers. In still another alternative embodiment of the invention, the unitary fabric structure is held together by an open bond pattern having low bond area. In yet another alternative, the composite is held together autogenously. In still another alternative embodiment, the unitary fabric structure composite is held together without the use of an individual adhesive layer. In still another alternative embodiment, the bond area of the composite is between about 5 and 15 percent. In yet another alternative embodiment, the components include hydrophilic fibers having no topical surfactants.

In yet another alternative embodiment, the unitary fabric structure includes a fibrous, core wrap functional component positioned immediately adjacent the fibrous, surge functional component, such that the fibrous, surge functional component is sandwiched between the fibrous, liner functional component and the fibrous, core wrap functional component. In another embodiment of the invention, the fibrous, core wrap functional component includes a structure that can serve as a barrier means to superabsorbent particle migration. In another alternative embodiment, the fibrous, surge functional component has a basis weight of between about 65 and 72 gsm. In another alternative embodiment, the fibrous, surge functional component has a basis weight of about 68 gsm. In still another alternative embodiment, the fibrous, core wrap functional component has a basis weight of between about 3 and 5 gsm. In yet another alternative embodiment, the fibrous, core wrap functional component is comprised of relatively small wettable fibers having a diameter of between about 2-6, and demonstrating an advancing contact angle of between about 40 and 60°. In another alternative embodiment, the fibrous, core wrap functional component includes no more than 3 gsm of 6$\mu$ or smaller dusting of fibers.

In another alternative embodiment, the fibrous, surge component itself includes at least two subcomponents, a first subcomponent including a mixture of relatively large diameter wettable fibers of between about 25 and 40$\mu$ and relatively small diameter wettable fibers of between about 8 and 18$\mu$, each of the wettable fibers demonstrating an advancing contact angle of between about 40 and 60°, and with some of the first subcomponent fibers including crimped, textured, curled or bent fibers, such that the first subcomponent has a density of between about 0.03 and 0.05 g/cc; and a second subcomponent adjacent the first subcomponent positioned on a side of the first subcomponent opposite to the fibrous, liner functional component, the second subcomponent including relatively small diameter wettable fibers of between about 8 and 18$\mu$ and demonstrating an advancing contact angle of between about 40 and 60°. In another alternative embodiment, the second subcomponent includes no more than 3 gsm of 6$\mu$ or smaller dusting of fibers. In another alternative embodiment, the first subcomponent has a basis weight of between about 50 and 55 gsm. In still another alternative embodiment, the first subcomponent itself is comprised of two components including a first, first subcomponent having a basis weight of between about 30 and 55 gsm and a second, first subcomponent having a basis weight of between about 0 and 25 gsm, and having smaller diameter fibers than the first, first subcomponent. Alternatively, the second, first subcomponent has an average pore size between fibers less than that of said first, first subcomponent. Alternatively, the second subcomponent has a basis weight of between about 10 and 15 gsm. Still in a further alternative embodiment, the second subcomponent itself is comprised of two components including a first, second subcomponent having a basis weight of between about 12 and 15 gsm and a second, second subcomponent having a basis weight of between about 0 and 3 gsm, and having smaller diameter fibers than said first, second subcomponent. Alternatively, the second, second subcomponent has an average pore size between fibers less than that of said first, second subcomponent.

In another alternative embodiment, the fabric structure has an X, Y and Z direction, wherein the fibrous, surge functional component includes a first surge functional component and a second surge functional component, the first surge functional component includes a mixture of relatively large diameter wettable fibers from between about 25 to 40µ, and relatively small diameter wettable fibers from between about 8 to 18µ, the wettable fibers having an advancing contact angle of between about 40 and 60°, the second surge functional component includes relatively small diameter wettable fibers, of between about 8 to 18µ and having an advancing contact angle of between 40 and 60°. In an alternative embodiment such first surge functional component has a basis weight of about 40 gsm. Alternatively, such first surge functional component includes two first surge subcomponents, a first, first surge subcomponent having between about 30 and 55 gsm basis weight, and a second, first surge subcomponent having between about 0 and 25 gsm basis weight and including smaller average diameter fibers than those contained in said first surge subcomponent. Alternatively, such first surge functional component includes progressively smaller fiber and pore sizes in the Z direction. Still alternatively, such second surge functional component has a basis weight of about 35 gsm. In yet another alternative, such second surge functional component includes two second surge subcomponents, a first, second surge subcomponent having a basis weight of between about 12 and 15 gsm and a second, second surge subcomponent having a basis weight of between about 0 and 3 gsm, and having smaller diameter fibers than said first, second surge subcomponent. In another alternative embodiment, the second surge functional component includes no more than 3 gsm of 6µ or smaller dusting of fibers.

In still another alternative embodiment of the invention, surge functional components of the unitary fabric structure include different levels of crimp in their respective fibers. In yet another alternative embodiment of the invention, each fibrous functional component is comprised of fibers having different structural/shape configurations.

A method for producing a unitary fabric structure for use within a personal care absorbent article, including a composite of at least two fibrous functional components for fluid intake, includes the steps of producing a fibrous, liner functional component from a first machine bank, producing at least one fibrous, surge functional component from at least a second machine bank, depositing one of the fibrous, functional components upon the other to form a composite; bonding or otherwise directly adhering, without the use of an adhesive layer, the fibrous, functional components to form a unitary fabric structure. In an alternative embodiment two surge functional components may be produced/utilized in the structure. In still a further alternative embodiment, a core wrap functional component may be produced/utilized in the composite structure. Such machine banks could produce or employ meltspun fibers in the functional components, of the types previously described.

In an alternative embodiment of a production method, the fibrous, liner functional component includes crimped, bent, curled or otherwise textured fibers. In another alternative embodiment of a production method, the fibrous, surge functional component includes crimped, bent, curled or otherwise textured fibers. In still a further alternative embodiment of the production method, the method further includes the steps of producing a second fibrous surge functional component from a third machine bank and depositing it upon the at least one fibrous, surge functional component prior to bonding or otherwise adhering the fibrous, functional components to form a unitary fabric structure. In another alternative embodiment of the production method, the first and second fibrous, surge functional components each include crimped, bent, curled or otherwise textured fibers, and further the crimped, bent, curled or otherwise textured fibers differ by surge functional component. In still another alternative embodiment of the production method, the method further includes the step of transporting such produced unitary fabric structure to a converting machine, wherein the unitary fabric structure is printed, slit, die cut, or otherwise processed for eventual inclusion into a personal care absorbent article.

In another alternative embodiment of the production method, the fibrous functional components are produced from fibers or materials selected from the group consisting of meltblown, spunbond, coform, airlaid, bicomponent, or biconstituent fibers and materials, or combinations thereof.

In another alternative embodiment, a method for producing a unitary fabric structure for use within a personal care absorbent article, the unitary fabric structure including a composite of at least three fibrous functional components for fluid intake, includes the steps of:
 a) producing a fibrous, liner functional component from a first machine bank;
 b) producing at least one fibrous, surge functional component from at least a second machine bank;
 c) producing at least one fibrous, core wrap functional component from at least a third machine bank;
 d) depositing the fibrous, surge functional component or components upon the fibrous, liner functional component;
 e) depositing the fibrous, core wrap functional component upon the fibrous, surge functional component or components;
 f) bonding or otherwise directly adhering without the use of an adhesive layer, all of the fibrous, functional components to form a unitary fabric structure.

In still another alternative embodiment, two fibrous, surge functional components are produced from two machine banks for incorporation into the unitary fabric structure. In still another alternative embodiment of the production method, the fibrous, core wrap functional component includes meltblown fibers. In yet another alternative embodiment of the production method, the first bank of machine is split so as to produce both a fibrous, liner functional component and a fibrous, surge functional component. In another alternative embodiment of the production method, the fibrous, liner functional component produced by the first bank of machine does not include crimped, curled, bent, or otherwise textured fibers, while the fibrous, surge functional component produced by the first bank of machine includes crimped, curled, bent or otherwise textured fibers.

In still another alternative embodiment of the production method, the fibrous, surge functional component produced by said second bank includes crimped, curled, bent or otherwise textured fibers. In another alternative embodiment, the produced fibrous, surge functional components include different levels of crimp in their respective fibers.

In yet another alternative embodiment, a method for producing a unitary fabric structure for use within a personal care absorbent article, the unitary fabric structure including a composite of at least two fibrous functional components for fluid intake includes the steps of:

a) producing a fibrous, liner functional component from a first machine bank;

b) producing at least one fibrous, surge functional component from at least a second machine bank, wherein the at least one fibrous, surge functional component is produced through a process imparting machine direction orientation;

c) depositing one of the fibrous, functional components upon the other to form a composite;

d) bonding or otherwise directly adhering, without the use of an adhesive layer, the fibrous, functional components to form a unitary fabric structure.

In an alternative embodiment, the first machine bank is split so as to produce both a fibrous, liner functional component and a fibrous, surge functional component. In still a further alternative embodiment, the method further includes the step of producing a meltblown web and depositing such web on the fibrous, surge functional component prior to bonding or otherwise directly adhering the fibrous functional components to form a unitary structure. In still a further alternative embodiment, the unitary fabric structure is placed in an absorbent article. In another alternative method each fibrous functional component is comprised of fibers of different chemical composition. In another alternative embodiment, each fibrous functional component is comprised of fibers having different structural/shape configurations. In still another alternative embodiment, a core wrap functional component includes meltblown fibers. In yet another alternative embodiment, the core wrap functional component includes meltblown and spunbond fibers. In a further alternative embodiment, the core wrap functional component spunbond fibers are positioned the farthest distance from the liner functional component in the Z direction.

Other features and aspects of the present disclosure are discussed in greater detail below.

Figure 1:
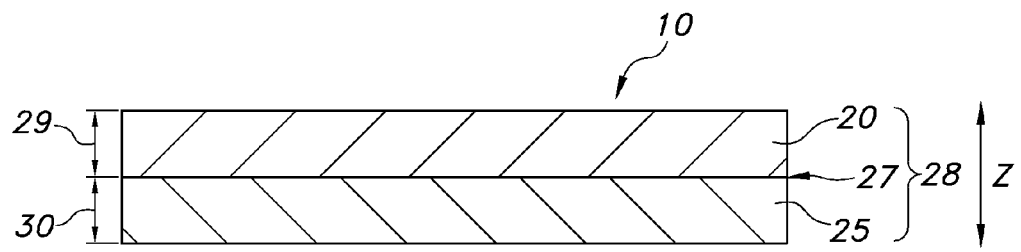
FIG. 1 is a cross-sectional view of a planar unitary fluid intake material system (unitary fabric structure) of the invention.

It is to be noted that repeat use of reference characters in the present specification and drawings is intended to represent same or analogous features or elements of the disclosure.

DETAILED DESCRIPTION OF THE INVENTION

Definitions

An "article" or "product" refers to a garment or other end-use personal care absorbent article of manufacture, including but not limited to, disposable diapers, training pants, swim wear, catamenial products, such as napkins, pads and panty liners, medical garments or wraps, and the like.

The term "bonded" or "bonding" refers to the joining, adhering, connecting, attaching, or the like, of two elements. As used herein "point bonding" means bonding one or more layers of fabric at a plurality of discrete bond points. For example, thermal point bonding generally involves passing one or more layers to be bonded between heated rolls such as, for example, an engraved pattern roll and a smooth calender roll. The engraved roll is patterned in some way so that the entire fabric is not bonded over its entire surface, and the anvil roll is usually flat. As a result, various patterns for engraved rolls have been developed for functional as well as aesthetic reasons. One example of a point bond pattern is the Hansen Pennings or "H&P" pattern with about a 30 percent bond area when new and with about 200 bonds/square inch as taught in U.S. Pat. No. 3,855,046 to Hansen and Pennings, incorporated by reference herein in its entirety. The H&P pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). Another typical point bonding pattern is the expanded Hansen Pennings or "EHP" bond pattern which produces a 15 percent bond area when new with a square pin having a side dimension of 0.037 inches (0.94 mm), a pin spacing of 0.097 inches (2.464 mm) and a depth of 0.039 inches (0.991 mm). Another typical point bonding pattern designated "714" has square pin bonding areas wherein each pin has a side dimension of 0.023 inches, a spacing of 0.062 inches (1.575 mm) between pins, and a depth of bonding of 0.033 inches (0.838 mm). The resulting pattern has a bonded area of about 15 percent when new. Yet another common pattern is the C-Star pattern which has, when new, a bond area of about 16.9 percent. The C-Star pattern has a cross-directional bar or "corduroy" design interrupted by shooting stars. Other common patterns include a diamond pattern with repeating and slightly offset diamonds with about a 16 percent bond area and a wire weave pattern looking as the name suggests, e.g. like a window screen, with about a 15 percent bond area. A further pattern is the "s-weave" pattern having about a 17 percent bond area when new and a baby objects pattern having about a 12 percent bond area when new. A further pattern still, is the Ramisch pattern which produces an 8 percent bond area when new with a square pin having a side dimension of 0.039 inches (0.991 mm) in a staggered array, a pin spacing of about 0.139 inches (3.53 mm) and a depth of 0.052 inches (1.321 mm). Such bonding patterns are further described in U.S. Pat. No. 5,599,420 to Yeo et al., incorporated by reference herein in its entirety. Typically, the percent bonding area is less than about 50 percent and more desirably varies from around 8 percent to around 30 percent of the area of the fabric web.

The term "disposable" refers to articles which are designed to be discarded after a limited use rather than being laundered or otherwise restored for reuse.

As used herein, the term "bicomponent fibers" refers to fibers which have been formed from at least two polymer sources extruded from separate extruders but spun together to form one fiber. Bicomponent fibers are also sometimes referred to as conjugate fibers or multicomponent fibers. The polymers are arranged in substantially constantly positioned distinct zones across the cross-sections of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement. Bicomponent fibers are taught by U.S. Pat. No. 5,108,820 to Kaneko et al., U.S. Pat. No. 4,795,668 to Krueger et al., U.S. Pat. No. 5,540,992 to Marcher et al., U.S. Pat. No. 5,336,552 to Strack et al., and U.S. Pat. No. 5,425,987 to Shawver, each being incorporated by reference in its entirety. Bicomponent fibers are also taught by U.S. Pat. No. 5,382,400 to Pike et al., incorporated by reference in its entirety. For two component fibers, the polymers may be present in ratios of 75/25, 50/50, 25/75 or any other desired ratio. Additionally, polymer additives such as processing aids, may be included in each zone.

The term "machine direction" (MD) refers to the length of a fabric in the direction in which it is produced, as opposed to a "cross-machine direction" (CD) which refers to the width of a fabric in a direction generally perpendicular to the machine direction.

A "meltblown fiber" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. which is incorporated by reference hereto in its entirety. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length. Webs produced by the meltblown process are generally referred to as meltblown materials or sometimes as meltblown.

For the purposes of this invention "dusting" of fibers is a relatively light deposit of relatively small fibers. Meltblown fibers are commonly used as dusting fibers.

"Spunbond fibers" refers to small diameter fibers that are formed by extruding molten thermoplastic material as filaments from a plurality of fine capillaries of a spinneret. Such a process is disclosed, for example, in U.S. Pat. No. 4,340,563 to Appel et al. incorporated by reference hereto in its entirety. The fibers also may have shapes such as those described, for example, in U.S. Pat. No. 5,277,976 to Hogle et al. which describes fibers with unconventional shapes (in the radial cross-section), incorporated by reference hereto in its entirety. Webs produced by the spunbond process are generally referred to as spunbond materials or sometimes simply as spunbond.

A "meltspun" fiber refers generically to a fiber which is formed from a molten polymer by a fiber-forming extrusion process, for example, such as are made by the meltblown and spunbond processes.

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns.

"Bonded carded web" refers to webs that are made from staple fibers which are sent through a combing or carding unit, which separates or breaks apart and aligns the staple fibers in the machine direction to form a generally machine direction-oriented fibrous nonwoven web. This material may be bonded together by methods that include point bonding, through air bonding, ultrasonic bonding, adhesive bonding, etc.

As used herein, the term "coform" means a process in which at least one meltblown diehead is arranged near a chute through which other materials are added to the web while it is forming. Such other materials may be pulp, superabsorbent particles (also known as SAP or SAM), natural fibers (for example, rayon or cotton fibers) and/or synthetic fibers (for example, polypropylene or polyester) fibers, for example, where the fibers may be short cut of staple length. Coform processes are shown in U.S. Pat. No. 4,100,324 to Anderson et al. and U.S. Pat. No. 4,818,464 to Lau, each incorporated by reference hereto in its entirety. Webs produced by the coform process are generally referred to as coform materials.

For the purposes of this disclosure, the terms "superabsorbent polymer," "superabsorbent", "SAP" or "SAM" shall be used interchangeably and shall mean polymers that can absorb and retain extremely large amounts of a liquid relative to their own mass. Water absorbing polymers, which are classified as hydrogels when cross-linked, absorb aqueous solutions through hydrogen bonding with water molecules. A SAP's ability to absorb water is a factor of the ionic concentration of the aqueous solution. SAPs are typically made from the polymerization of acrylic acid blended with sodium hydroxide in the presence of an initiator to form a poly-acrylic acid sodium salt (sometimes referred to as sodium polyacrylate). Other materials are also used to make a superabsorbent polymer, such as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. SAPs may be present in absorbent articles in particle or fibrous form.

"Airlaying" is a well-known process by which a fibrous nonwoven layer can be formed. In the airlaying process, bundles of small fibers having typical lengths ranging from about 3 to about 52 millimeters (mm) are separated and entrained in an air supply and then deposited onto a forming screen, usually with the assistance of a vacuum supply. The randomly deposited fibers then are bonded to one another using, for example, hot air to activate a binder component or a latex adhesive. Airlaying is taught in, for example, U.S. Pat. No. 4,640,810 to Laursen et al. incorporated by reference hereto in its entirety.

In general, the present invention is directed to a unitary fabric structure in which a single composite fabric can replace the multiple fabric layers that have historically been placed in personal care absorbent articles to provide different functionality. For the purposes of this disclosure, the term "unitary" shall refer to a self-supporting composite fabric that includes "at least two functional components," and which composite is bonded together as a single planar sheet without the use of a separate adhesive layer between the functional components. Essentially, the "at least two functional components" are directly attached, bonded or otherwise adhered to one another, such as through pressure, heat, ultrasonic, hydroentanglement, or autogenous bonding methods. Essentially, the components are closely nested with the elimination of most observable gaps, to allow for the intake and movement of fluid more readily. For the purposes of this application, autogenous bonding shall refer to a type of bonding without use of a separate adhesive layer, in which fibers are bonded to one another based upon the chemical formulations of the individual fibers. Such fibers are either inherently tacky, or become tacky upon the occurrence of a secondary event, such as for example, application of heat or pressure to soften or melt a component in an otherwise non-tacky fiber. In a further embodiment, such unitary fabric structure includes at least three functional components. Desirably such unitary fabric structure is bonded together in one production step, such as by, pressure, thermal pressure, ultrasonic or through-air bonding techniques. The unitary fabric structure is bonded so as to create such self-supporting attribute, following the deposit of the at least two functional components upon one another desirably, from a series of meltspinning machine banks. The fibrous functional components are desirably selected from meltblown, spunbond, staple, and/or coformed fibrous materials. In one embodiment, it is desirable that such fibrous components include hydrophilic fibers, such as hydrophilic fibers without topical surfactants. Desirably, the materials are point bonded with an open pattern, having relatively low bond area. Such low bond area helps to prevent the crushing of the functional components and retains bulk. An example of a desirable bond pattern is described in U.S. Pat. No. 4,863,785 to Berman et al., which is hereby incorporated by reference. Other relatively low bond area patterns have been previously noted.

The components of the unitary fabric structures are not individually manufactured self supporting sheets (ie. they are not self supporting sheets that are produced at separate locations or at separate times) that are brought together in one or more lamination steps, but are rather produced as part of a single manufacturing process in-line from multiple machine banks in sequence, or in a single machine having multiple banks, with one component deposited upon another. The entire composite is eventually bonded directly together, following the deposition of all components immediately adjacent one another, without being separated by intermediate adhesive layers. Following manufacture, the unitary fabric structure may be stored, such as on rolls, or alternatively, directly passed to product conversion processes, such as to a printing station, die cut station, slitting station, or other product conversion station, for eventual inclusion into a personal care absorbent article.

In one embodiment of the inventive unitary fabric structure, a composite with liner and surge functionality is provided. Desirably, the liner and surge functional composite demonstrates bulk, high void volume, and at least modest internal fluid spreading capability. The composite includes a first component (the fibrous, liner functional component) with a relatively smooth surface for contact with a user's skin and which allows rapid fluid penetration, but which does not retain residual fluid. Such material desirably includes between about 10 and 18 micron ($\mu$) hydrophilic or hydrophilically treated fibers, alternatively between about 12 and 18$\mu$, further alternatively between about 15 and 18$\mu$, demonstrating an advancing contact angle of between about 75 and 80°. For the purposes of this application, it is desirable for such hydrophilicity to be imparted to the fiber materials via incorporation of wetting agents into the fiber polymer mix or by use of inherently wettable polymers, rather than topical treatment of a surfactant, such that durable wettability is provided to the fibers, and further so as to avoid loss of such chemistry during fabric and product manufacture. Such fibrous material desirably includes no more than 2 gsm of 6$\mu$ (or smaller) dusting of fibers for opacity or other benefits. For the purposes of this application, such advancing contact angles are desirably measured using Wilhelmy Wetting Force Principle instruments. Such principles are known and described further in *Absorbency*, edited by Pronoy K. Chatterjee, Elsevier Science Publishing Company Inc. New York, 1985, Page 125. Further general description of hydrophilic fibers and contact angle measurements may be found in U.S. Pat. Nos. 5,364,382 and 5,429,629 to Latimer et al.

Single fiber contact angle measurements are commonly quantified. One such instrument for conducting this work is the Attension Sigma 701 Force Tensiometer. Attension is one of the product organizations within the Biolin Scientific group (www.biolinscientific.com). Procedural instructions for using the instrument are explained in Chapter 8 "Dynamic Contact Angle Measurement" of the Operation Manual. The instrument was set up with the default testing conditions as recommended in the Operation Manual (such as a speed of 50 mm/min in both the up and down cycles and utilized an immersion depth of 10 mm).

As practiced, individual fibers may be tested through three measurement cycles. One end of a fiber is placed in the center of a strip of kitchen aluminum foil (about 2 cm×4 cm) and the foil is folded over the fiber end and sealed using the serrated crimping teeth of hand-held forceps. The aluminum foil acts as a hooking element to ensure the fiber remains perpendicular to the upper plane of the fluid during testing. The foil hangs on the balance hook. The opposite fiber end is introduced to the test fluid bath. Testing is conducted using a 50 ml beaker of room temperature (about 72° F./22° C.) distilled water. The water bath is changed after each measurement. It is desirable for a fiber to meet the specification range for advancing contact angle on all three measurement cycles.

In one embodiment it is desirable for the basis weight of the first component (liner functional component) to be about 3-10 gsm, alternatively about 6 gsm and include between about 4 and 6 gsm of relatively larger fibers (>10 microns diameter per filament) and between about 0 and 2 gsm relatively small fibers (<10 microns diameter per filament). Such fibers may for example, include meltspun materials such as spunbond and meltblown depositions, but it is desirable for such first component to be produced using one machine bank.

The unitary fabric structure includes a second component (the fibrous surge functional component) that wets readily, decelerates and spreads fluid within the structure, and which substantially releases fluid to an absorbent core layer, while maintaining void volume for subsequent fluid insults. Desirably, such second component is a mixture of relatively large (25-40 micron fiber diameter) and relatively small (8-18 micron) diameter fibers that are wettable fibers (having an advancing contact angle of between about 40 and 60°).

Desirably such fibers are produced from one machine bank (the second in a series) and with crimp, texture, curls or bends to prevent fiber packing and achieve a bulky, low density structure (of desirably between about 0.03-0.05 g/cc). The fibers of the first component and the second component (and the remaining functional components described herein) are desirably selected from polyester, polyamide, permanently wettable hydrophilic polyolefins, polylactic acid (PLA), homopolymers as well as bicomponent and biconstituent fibers containing such polymers.

In a second embodiment, such unitary fabric structure includes a fibrous, liner functional component, a fibrous, surge functional component, and a fibrous core wrap, functional component. Desirably such fibrous surge functional component includes crimped, curled, bent or otherwise textured fibers. Such fibrous, liner functional component is desirably smooth and gentle for contact with the skin of a user, and allows for rapid fluid penetration with little retention of residual fluid. The fiber composition (both physical attributes and chemical makeup) of the liner functional component, is desirably as described with respect to the previous embodiment. Likewise, the fibrous, surge functional component is also as described with respect to the prior embodiment. Alternatively, such fibrous, surge functional component may itself include multiple components with progressively smaller fibers and pore structures in the Z-direction of the composite, the smaller fibers and pores being located farther from the liner functional component. Desirably in one embodiment, such surge functional component has a basis weight of about 63-78 gsm, alternatively about 68 gsm.

The fibrous, core wrap functional component desirably distributes fluid in the X-Y plane, and releases fluid to a core layer when placed in an absorbent article, but which also provides barrier properties so as to inhibit superabsorbent particle migration back to the fibrous, liner functional component exposed surface from a core layer. Desirably in one embodiment, such fibrous, core wrap functional component includes small diameter wettable fibers, of between about 8-18 micron diameter and demonstrating an advancing contact angle of between about 40 and 60°. In one embodiment, such core wrap functional component includes no more than about 3 gsm of 6μ or smaller dusting of fibers. Such material desirably demonstrates a relatively high density and relatively small pore size, and has a basis weight of between about 3 to 5 gsm.

In yet a further alternative embodiment, a unitary fabric structure includes a fibrous, liner functional component and a fibrous, wicking-surge functional component. The wicking-surge component desirably demonstrates modest void volume and rapid fluid spreading properties. As with the prior embodiments, the fibrous, liner functional component includes similar fibers to those previously described for liner functional components. However, the fibrous, surge functional component is in an alternative embodiment a two surge functional component structure. A first surge functional component, located immediately adjacent the fibrous, liner functional component is a mixture of large (about 25-40 micron diameter) and small (8-18 micron diameter) and wettable (about 40-60° advancing contact angle) fibers. Such fibers desirably include crimp, curl, bends or other textures to prevent fiber packing and achieve a bulky, low density (about 0.03-0.05 g/cc) structure. Such first surge component desirably has a basis weight of between about 50 and 55 gsm and includes fibers of the type described for the surge component of the previous embodiment. The first surge component, may alternatively, itself be comprised of two subcomponents, the first subcomponent having a basis weight of between about 30 and 55 gsm and the second subcomponent having a basis weight of between about 0 and 25 gsm, and having smaller diameter fibers than the first subcomponent.

The second surge functional component desirably has a basis weight between about 10 and 15 gsm. Such second surge functional component desirably includes small (8-18 micron diameter) and wettable fibers (40-60° advancing contact angle), that may include the option of no more than 3 gsm of 6μ or smaller dusting of fibers. It is desirable of relatively high density and relatively small pore size. Like the first surge functional component, it too may also be comprised of two subcomponents, with a first subcomponent having a basis weight of between about 12 and 15 gsm and the second subcomponent having a basis weight of between about 0 and 3 gsm, with smaller diameter fibers than the first subcomponent, the smallest fibers positioned the farthest from the fibrous, liner functional component in the Z direction.

In yet a further alternative embodiment, the unitary fabric structure may include a fibrous, liner functional component and a fibrous, wicking surge functional component where the wicking surge component demonstrates rapid fluid spreading. In such embodiment, the fibrous, liner functional component would be the same as previously described embodiments. However, the wicking-surge functional component would in a first embodiment, include a first surge component having a basis weight of about 40 gsm and include previously described surge functional fibers. The wicking surge would also include a second surge component having a basis weight of about 35 gsm and include small (8-18 microns) diameter, wettable (40-60° advancing contact angle) fibers, that may optionally include no more than 3 gsm of 6μ or smaller dusting of fibers. Desirably, such second surge component is of relatively high density and demonstrates relatively small average pore size. Alternatively, the first surge component is itself in one embodiment, made up of two first surge subcomponents, including a first subcomponent having a basis weight of between about 30 and 55 gsm and a second surge subcomponent having a basis weight of between 0 and 25 gsm with smaller diameter fibers than the first surge subcomponent. Alternatively, the second surge component is also made up of two subcomponents, including a subcomponent having a basis weight of between about 12 and 15 gsm and a subcomponent having a basis weight of between about 0 and 3 gsm, with smaller diameter fibers than the first subcomponent. The smallest fibers in the surge layer (in this and previous embodiments) are desirably the farthest distance from the fibrous, liner functional component in the Z direction.

It should be understood that such unitary fabric structures may be manufactured using numerous methods. The below described methods can be practiced in a single machine (having multiple banks or beams, such as multiple banks of the meltspinning techniques noted herein) or in a series of multiple connected in-line machines having multiple banks or beams. The bank or beam arrangement can be in the sequence described, or alternatively in a reverse sequence, in order to produce the planar unitary fabrics. The banks can be used to produce and deposit continuous fibers or discontinuous fibers (such as staple fibers) of one functional component upon another before bonding of the whole composite (without a separate adhesive layer) into a unitary fabric structure. The unitary fabrics then can be stored, or immediately directed to a conversion process for placement into disposable products as previously described. For example, such unitary fabric structures may be immediately transported to printing, die cutting, slitting or other processing stations, or saved for later use.

In a first embodiment of a production method, a two or three bank machine may be utilized to produce a liner and surge functional component, unitary fabric structure. In such a method a fibrous, liner functional component is produced from a first bank. The liner functional component may include crimped or non-crimped/textured fibers. Following production of such fibrous, liner functional component, a produced fibrous, surge functional component made from a second machine bank, can be deposited directly on the fibrous, liner functional component to produce a composite, and then the composite of two components may be bonded or otherwise adhered, without the use of a separate adhesive layer, such that the unitary fabric structure is produced. The fibrous, surge functional component may include crimped fibers for bulk. Alternatively, three machine banks may be used to produce the unitary fabric structure, with the third bank used to produce a second fibrous, surge functional component on the first fibrous, surge functional component. In such embodiment, the liner component may include crimped or noncrimped fibers, and the two surge components produced on the second and third machine banks may each include different crimped fibers. In yet another alternative embodiment, the first machine bank which is used to produce the fibrous, liner functional component may be split such that it produces and deposits a non-crimped liner functional component and a crimped surge functional component, while the second machine bank produces and deposits a crimped surge functional component. In such an embodiment, the first machine bank which is used to produce the fibrous, liner functional component is configured as a "split bundle", such that the one section of the fiber bundle produces a non-crimped liner functional component and the other section of the fiber bundle produces a crimped surge functional component which are simultaneously deposited and partially integrated on the webformer, while the second machine bank produces and deposits a crimped surge functional component.

In a second embodiment of a production method, a fibrous liner, surge and core wrap functional component are produced as part of a unitary fabric structure. In such an arrangement, a first machine bank may be used to produce a fibrous, liner functional component or alternatively as a "split bundle" (as described above) to produce a fibrous, liner functional component and a fibrous, surge functional component. A second machine bank may be used to produce a fibrous, surge functional component, while a third machine bank may be used to produce either a fibrous, core wrap functional component (such as for example a meltblown web), or alternatively a second fibrous, surge functional component. In an alternative embodiment, a fourth machine bank may be used to produce a fibrous, core wrap functional component for a two surge functional component system. It should be understood that each bank produces and deposits its respective functional component on top of the previous bank's produced component before a final bonding step of the composite to produce the unitary fabric structure. In those systems in which multiple surge functional components are employed, different levels of crimp and different crimped fibers may be employed in order to create gradient crimp levels.

In a third embodiment of a production method, a fibrous, liner functional component and a fibrous, wicking surge/intake functional component can be produced from between two and four machine banks before being bonded. Desirably, the fibrous, wicking surge/intake functional component demonstrates machine direction orientation of the fibers during the formation process. In one alternative of such a combination, a fibrous, liner functional component may be produced and deposited from a first machine bank. An adjacent second machine bank may then be used to produce and deposit a fibrous, wicking surge functional component. Optionally, a third machine bank may be used to then deposit an additional meltblown-based component upon the fibrous, wicking surge functional component so as to further improve wicking performance of the unitary fabric structure. In another alternative of the embodiment, a first machine bank may be used to produce and deposit a fibrous, liner functional component. A second machine bank may be used to produce a fibrous intake surge functional component and deposit it upon the liner functional component. A third machine bank may then be used to produce a fibrous wicking surge functional component and deposit it upon the fibrous intake surge functional component. An optional fourth machine bank may then be used to produce and deposit a meltblown-based wicking layer upon the fibrous intake surge functional component. Still in another alternative, instead of producing two different types of surge components (such as an intake surge, without the necessity of machine direction oriented fibers, and a wicking surge, with machine direction oriented fibers), two of the same surge components, such as two wicking surge components may be produced by two machine banks.

It should be recognized that during the methods of production of the unitary fabric structure described above, either the respective machine banks can themselves be moved to produce the respective fibrous components over a stationary carrier holding the deposited components, or alternatively, the deposited components may be deposited onto a moving carrier, such as a sheet or forming wire which transports the deposited components between banks, and which will eventually be used to transport the multicomponent composite to a bonding station, where it can be bonded without the use of separate adhesive layers. The multicomponent composite may then be exposed to any of the previously described bonding techniques, such as for example, a roll-based, point bonding station, a through-air (such as heated air) bonding station, or an ultrasonic bonding station. The formed unitary fabric structure then may be transported to a winding station, or alternatively directly transported to a product conversion area. During production of the various components from the respective machine banks, it should be recognized that various fiber types (with different physical attributes) and fiber compositions can be employed to enhance desired fabric structure, such as to create gradients, loft, or enhanced wicking. For example, fibers having various radial cross-sections, as previously described, may be used to enhance wicking in particular directions. Further, if methods of production are to include point bonding of the composite, it is desirable in one embodiment to have a spunbond component closest to the point of impact of points of the bonding roll. In a further embodiment, it is desirable for a core wrap functional component to include both meltblown and spunbond fibers, with spunbond fibers positioned the farthest from the liner functional component in the Z direction.

Description of Figures

Figure 2:
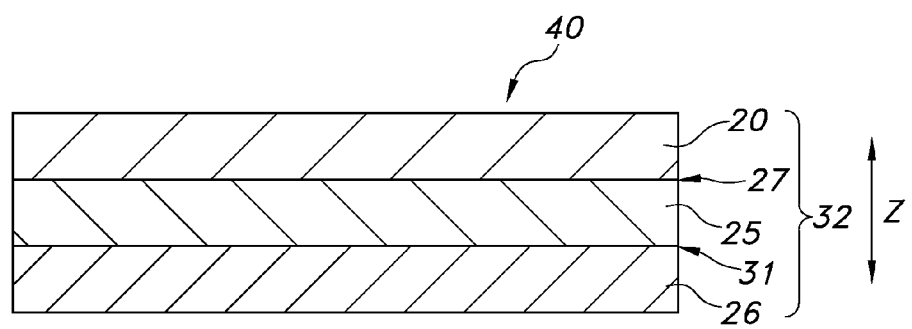
FIG. 2 is a cross-sectional view of an alternative embodiment of the planar unitary fluid intake material system of FIG. 1.
Figure 3:
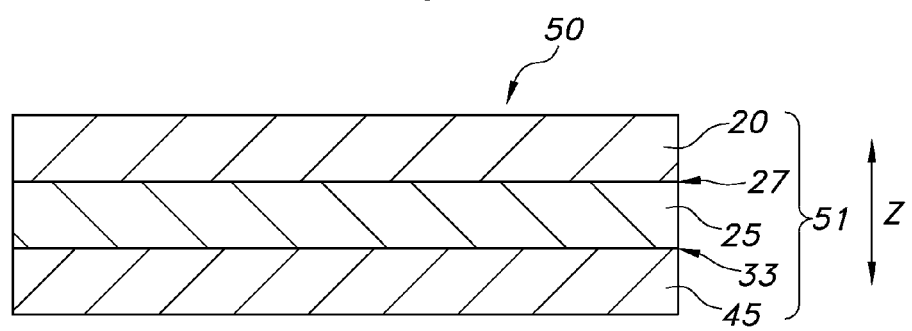
FIG. 3 is a cross-sectional view of another alternative embodiment of the planar unitary fluid intake material system of FIG. 1.

In order to further illustrate the unitary fabric substrate embodiments of the planar unitary fluid intake system, the unitary fabric substrate of the invention is shown in FIGS. 1-3. As can be seen in cross-sectional view in FIG. 1, a two functional component composite 10 is shown having a Z direction (depth). The two functional component composite includes a fibrous, liner functional component 20 having a thickness 29, and a fibrous, surge functional component 25 having a thickness 30. The two functional components are in direct contact along their interface 27, following deposition of one upon the other and the composite exposed to bonding. The overall composite has a thickness 28 as well, which thickness is desirably less than that which would be present for traditional separately produced layers that would have been laminated by a separate adhesive layer. By employing the inventive formation methods, the thicknesses and basis weights of the respective components 29, 30 may if desired, be significantly less than those of separately produced and provided layers, thereby resulting in less overall mass.

FIG. 2 illustrates a cross-sectional view of an alternative embodiment of the planar, fluid intake-directed, unitary fabric structure. As can be seen in the Figure, a unitary fabric structure 40 is illustrated with three components rather than two. The fibrous, liner functional component 20 is deposited adjacent a first fibrous, surge functional component 25 at interface 27. However, a second fibrous, surge functional component 26 is also deposited at interface 31 for direct contact with the first, fibrous, surge functional component 25. As an example, such first and second surge functional components may be of the same fibrous materials, or of different fibrous materials. Specifically, the first and second surge functional components may be both wicking surge functional components (as previously described), or alternatively, may be of an intake surge functional component and a wicking surge functional component. The overall composite has a thickness 32 that would desirably be less than the historical thicknesses of separately produced, separately bonded and then adhesively joined layers. At least the mass of two separate adhesive layers are missing in this unitary fabric structure.

FIG. 3 illustrates a cross-sectional view of a further alternative embodiment of the planar, fluid intake-directed, unitary fabric structure. In this embodiment, a three functional component fluid intake system is illustrated 50, which includes a fibrous, liner functional component 20 adjacent a fibrous, surge functional component 25 at interface 27. A fibrous, core wrap functional component 45 is adjacent the fibrous, surge functional component at interface 33. The overall composite 50 has an overall thickness 51 and basis weight, that is desirably less than that of separately produced and later united layers.

Figure 4:
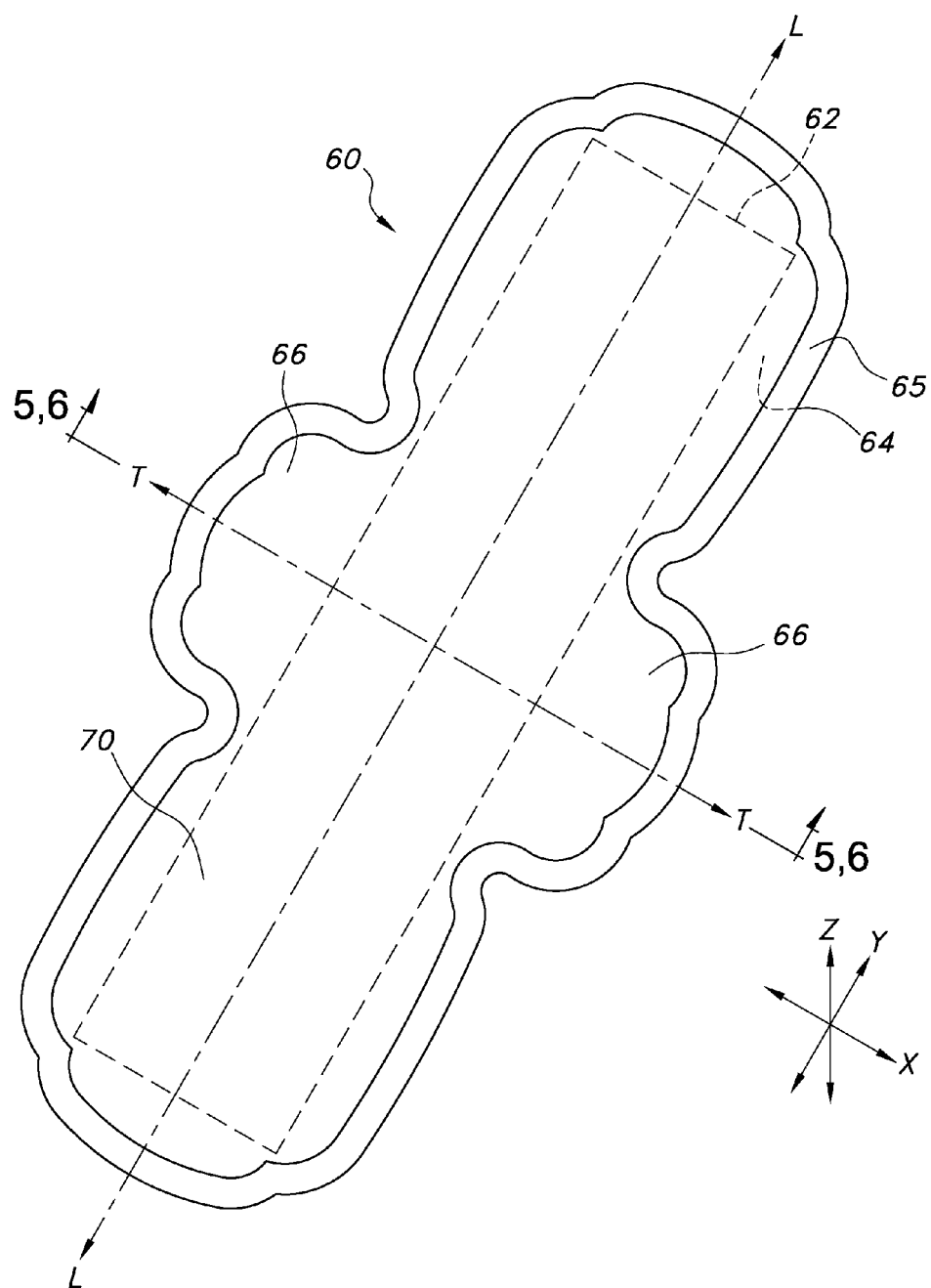
FIG. 4 is a top perspective view of a personal care absorbent article in the form of a feminine care hygiene article (pad) utilizing a planar unitary fluid intake material system of the invention.

FIG. 4 illustrates use of a unitary fabric structure of the invention in an absorbent article, and in particular, a feminine care hygiene article such as a pad 60. Disposable personal care absorbent articles often share similar structural components, and as such, all classes of absorbent articles will not be shown. However, it should be understood that the unitary fabric structure of the invention can be used in numerous types of personal care absorbent articles, as previously described. Absorbent articles, like the one illustrated, often include a fluid permeable topsheet or liner layer, having a user skin-facing surface 62. The topsheet is desirably soft and may be treated, or otherwise designed to be wettable. A fluid impermeable backsheet layer (or baffle) 63, having a garment facing surface 64 (in FIG. 5), is often bonded to the liner layer along the periphery of the article 65. The fluid impermeable backsheet layer 63 provides a barrier to stop the leakage of fluid out of the article, and onto a user's garments or bedding. Such backsheet layer may be breathable, and is often constructed of polymeric film or other barrier materials. An absorbent core layer 70 is enclosed between the liner layer and the backsheet layer for retaining absorbed fluids that enter the article through the liner layer. The absorbent core layer often includes superabsorbents and cellulosic materials, may be constructed primarily of cellulosic materials, alternatively, may be constructed of high retention synthetic materials, or alternatively may be a combination of cellulosic materials and synthetic fibrous materials. As seen in the figure, such articles typically have a longitudinal direction L (along a Y axis) and a transverse direction T along an X-axis. The articles also have a depth direction along the Z axis.

Figure 5:
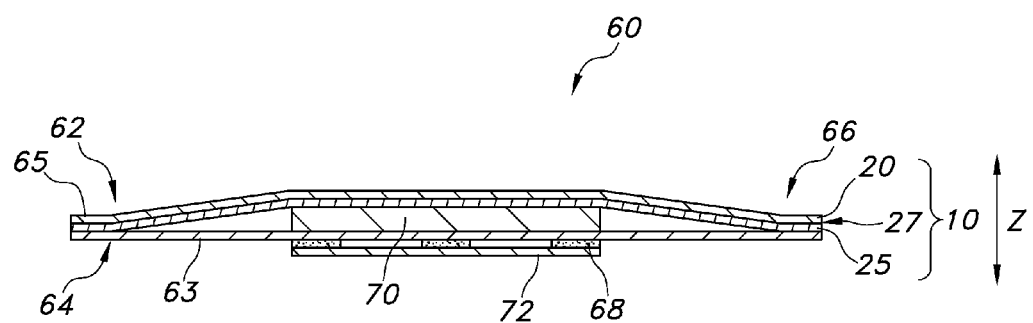
FIG. 5 is a cross-sectional view of the personal care absorbent article of FIG. 4 taken along lines 5-5.

Optionally, such feminine care pads may include wing-like flap structures 66 for attachment of the article to a user's undergarments. Such wing-like flap structures are often extensions of the liner and backsheet layers along the transverse direction of the article. Such may be integral extensions as shown, or separately attached structures. The pad illustrated includes garment attachment adhesive patches 68 along the backsheet 63 underside (on the garment facing surface 64 (as seen in FIG. 5), for fastening of the article to a user's undergarments. Such patches may be located on the underside of the wing-like flaps 66, or alternatively along the center longitudinal direction L of the backsheet layer 63, garment facing surface 64. Typically, adhesive patch covers or release sheets, 72 are placed over the adhesive patches for protection and preservation of the adhesive prior to use.

Such an absorbent article may include a separate surge or fluid intake layer positioned between the liner layer and the absorbent core layer, for handling and transferring sudden surges of fluid from a user that are deposited on the liner layer, and flowing into the absorbent core layer. If the absorbent article includes superabsorbent or smaller fibers/particles within the absorbent core layer 70, it is also common for such article to include an enveloping sheet that completely or partially encircles (like a "C" or "U") the dimensions of the absorbent core layer 70 so as to provide a barrier that prevents the release of the superabsorbent or other particles from the core layer 70 to the outside of the article 60.

A cross-sectional view of FIG. 4 is illustrated in FIG. 5, taken along line 5-5. As can be seen in the figure, the unitary fabric structure 10 has been placed in the article, and provides both liner component functionality 20, and surge component functionality to the article 60. Such unitary fabric structure 10, extends in one embodiment, along the same longitudinal L and transverse T directions/dimensions as the backsheet layer 63 and is in fact bonded along the peripheral edges 65 to the backsheet layer 63. Such unitary fabric structure sits over the absorbent core layer 70.

Figure 6:
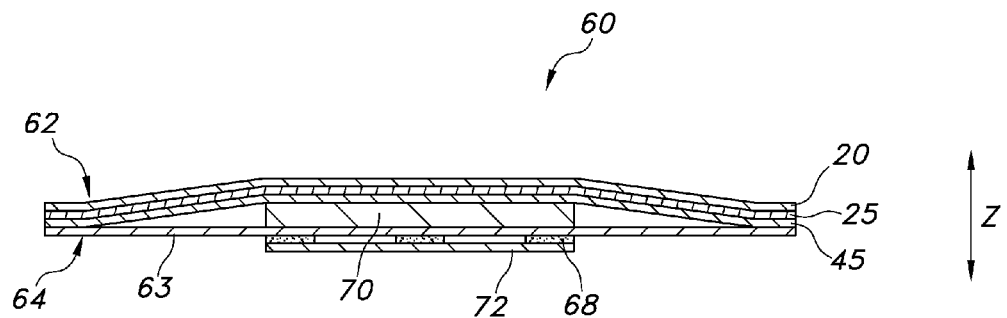
FIG. 6 is a cross-sectional view of an alternative embodiment of the personal care absorbent article of FIG. 4 taken along lines 6-6.

In an alternative embodiment of FIG. 4, as shown in cross-sectional view in FIG. 6 taken along lines 6-6 of FIG. 4, a unitary fabric structure including a liner functional component 20, a surge functional component 25 and a core wrap functional component 45 is illustrated. As with the previous embodiment, such unitary fabric structure extends in one embodiment, along the same longitudinal L and transverse T directions/dimensions as the backsheet layer 63 and is in fact bonded along the peripheral edges 65 to the backsheet layer 63. Such unitary fabric structure sits over the absorbent core layer 70. In such a fashion, the absorbent core layer 70 has a barrier protecting it from unwanted leakage of superabsorbent materials to the outside of the product.

Figure 4A:
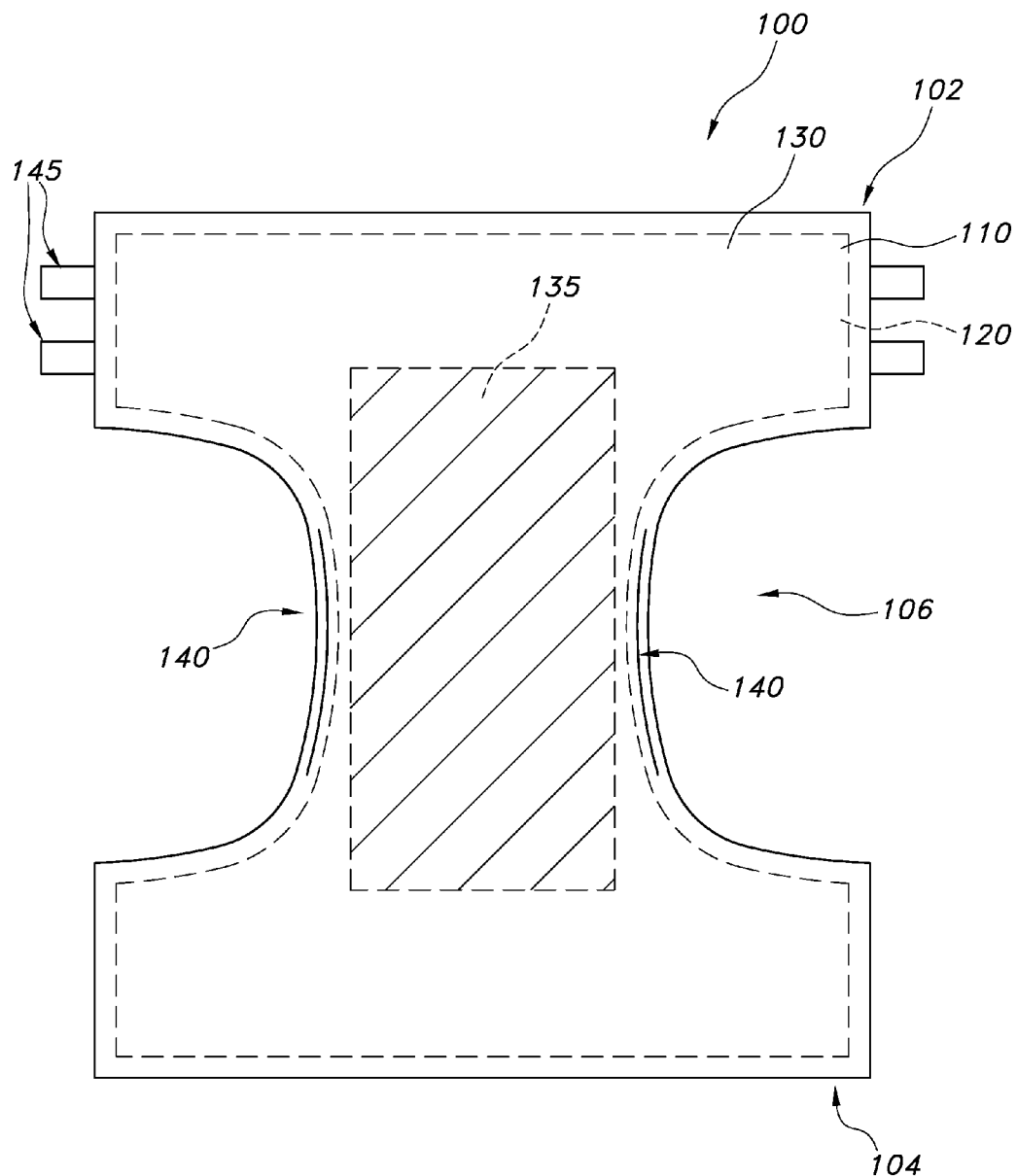
FIG. 4A is a top plan view of a personal care absorbent article in the form of a baby/child care diaper utilizing a planar unitary fluid intake material system of the invention.

In an alternative embodiment of the invention, a unitary fabric structure is placed in a baby/child care absorbent article in the form of a diaper. As seen in FIG. 4A, a diaper 100 is illustrated having first waist region 102 and a second waist region 104, which waist regions are connected via a crotch region 106. Like the previously illustrated feminine hygiene article, the diaper 100 includes a liquid permeable topsheet or liner layer 110 and a liquid impermeable backsheet or baffle layer 120. The backsheet layer may be breathable if desired. An absorbent core layer 135 is sandwiched between the topsheet layer 110 and the backsheet layer 120. The absorbent structure includes at least a surge layer 130 as well, situated between the topsheet layer and the absorbent core layer. The interiorly situated surge layer and absorbent core layer may be of the same dimensions along the article longitudinal or transverse directions or of different dimensions as shown. The absorbent core layer can also include a core wrap as previously described. The diaper 100 also includes leg elastic materials 140 to assist in maintaining a snug fit about the user's legs in the crotch region, and fastening means 145 to assist in securing the waist portions. As noted in connection with the feminine hygiene article, the inventive unitary structure can be used as a topsheet layer and underlying surge layer, as a topsheet layer, underlying surge layer and core wrap, or alternatively, as a surge layer and corewrap layer.

The unitary fabric structure is produced using an in-line manufacturing process (for example, in-line with one functional component formed upon one another to create an integral structure), as opposed to from multiple distinct/separated manufacturing processes that are then brought from the separated manufacturing equipment, have been separately bonded for integrity, and then bonded with the use of distinct adhesive layers to join the separately produced layers. For a unitary fabric structure of the present invention, various functional components are integrated into one composite during an initial manufacturing process, such that the combination of functional components desirably results in an overall basis weight reduction in fabric versus traditional functional, separately produced layers of absorbent products that are merely placed one atop another. Such a unitary fabric structure may be employed within a personal care absorbent article for example, as a liner and surge composite fabric structure, as a liner, surge and core wrap composite fabric structure, or alternatively, as a surge and core wrap composite fabric structure.

The unitary fabric structure of the present invention can replace individual fabric layers which have historically served as separate liner, surge, intake, fluid acquisition, wicking, distribution or core wrap layers. The unitary fabric structure combines the numerous performance functions of these various layers into one composite having the same or better functional performance, desirably in one embodiment, at lower overall mass. As a result, the number of fabric layers and adhesive quantity generally employed to hold such layers together in absorbent articles is reduced. Such a unitary fabric structure eliminates the need for additional manufacturing processes that would normally be necessary to convert multiple functional layers into a single product. Such a unitary structure is desirably also thinner than multiple bonded layers having different functions, and may be more flexible depending on the embodiment, when compared to historical personal care absorbent article layers of fabric and adhesive. The specific design of the unitary fabric structure yields a functionally beneficial and mass-efficient composite material.

The unitary fabric structure of the present invention addresses problems associated with interlayer connectivity that are common for separately produced layers that are laminated together with adhesive. The spatial gaps at the interface of adhesively bonded, separately produced layers are eliminated or reduced. Further, the use of separate layers of adhesive is also eliminated, thereby reducing stiffening elements and fluid pathway obstructions that are created by such (often hydrophobic) adhesive layer(s). The unitary fabric structure eliminates the need for use of separate core wrap layers and the accompanying adhesive. As a result of this functional improvement, the need for small diameter fiber (usually meltblown fiber) core wraps is eliminated. Fluid is guided from one layer to another, and eventually to the core layer, thereby maintaining skin dryness, with little fluid residue on the product surface at the user's skin.

The mass efficiency of a unitary structure is achieved by using only as much mass for each functional component as required by the fluid handling role. The functional role of a liner component in the unitary fabric structure includes providing gentle skin contact, providing adequate strength in product converting and use, and the prevention of construction adhesive and other interior layer components from migrating back to the skin of a user. The functional role of the surge layer component is to accept rapid fluid intake (with only short term/temporary fluid holding capability), horizontal fluid spreading and distribution, and significant fluid release to a core layer. The functional role of the core wrap functional component is to serve as a barrier to superabsorbent migration out of the product, with each of the layers held in a composite structure without separate adhesive layers.

The present invention has been described in general and in detail by means of examples. Persons of skill in the art understand that the invention is not limited necessarily to the embodiments specifically disclosed, but that modifications and variations may be made without departing from the scope of the invention as defined by the following claims or their equivalents.

We claim:

1. A unitary fabric structure for use within a personal care absorbent article comprising:
    a composite of at least two functional components for fluid intake, wherein said two functional components include a fibrous, liner functional component and at least one fibrous, surge functional component, said functional components positioned immediately adjacent one another within said composite and held together directly in facing contact with one another;
    wherein said fibrous, liner functional component is comprised of hydrophilic fibers including first and second fibers, said first fibers having diameters between 10 and 18μ and a basis weight between about 4 and 6 gsm, and said second fibers having fiber diameters less than 10μ and a basis weight less than 2 gsm.

2. The unitary fabric structure of claim 1 wherein said fibrous, liner functional component is comprised of hydrophilic fibers demonstrating an advancing contact angle of between about 75 and 80°.

3. The unitary fabric structure of claim 1, wherein said fibrous, liner functional component has a basis weight of about 6 gsm.

4. The unitary fabric structure of claim 1, wherein said fibrous, surge functional component comprises a mixture of wettable third fibers having a size of between about 25 and 40 micron fiber diameter, and wettable fourth fibers having a size of between about 8 and 18 microns, and said third and fourth fibers demonstrating an advancing contact angle of between about 40 and 60°.

5. The unitary fabric structure of claim 4, wherein said mixture of said third and fourth fibers includes fibers demonstrating either crimp, texture, curl, bends or combination thereof, such that said fibrous, surge functional component demonstrates a density of between about 0.03 and 0.05 g/cc.

6. The unitary fabric structure of claim 1, wherein said composite is held together by an open bond pattern having a bond area of between about 5 and 15%.

7. The unitary fabric structure of claim 1, wherein said composite is held together autogenously.

8. The unitary fabric structure of claim 1, further including a fibrous, core wrap functional component positioned immediately adjacent said fibrous, surge functional component, such that said fibrous, surge functional component is sandwiched between said fibrous, liner functional component and said fibrous, core wrap functional component.

9. The unitary fabric structure of claim 8, wherein said fibrous, core wrap functional component includes a structure that can serve as a barrier means to superabsorbent particle migration.

10. The unitary fabric structure of claim 8, wherein said fibrous, core wrap functional component is comprised of relatively small wettable fibers having a diameter of between about 2-6 microns, and demonstrating an advancing contact angle of between about 40 and 60°.

11. The unitary fabric structure of claim 10, wherein said fibrous, core wrap functional component includes no more than 3 gsm of 6μ or smaller dusting of fibers.

12. The unitary fabric structure of claim 1, said fabric structure having an X, Y and Z direction, wherein said fibrous, surge functional component includes a first surge functional component and a second surge functional component, said first surge functional component including a mixture of wettable third fibers having a size from between about 25 to 40 microns diameter, and wettable fourth fibers having a size from between about 8 to 18 microns diameter, the third and fourth wettable fibers having an advancing contact angle of between about 40 and 60°, said second surge functional component including wettable fifth fibers, having a size of between about 8 to 18 microns diameter and having an advancing contact angle of between 40 and 60°.

13. An absorbent article comprising the unitary fabric structure of claim 1, wherein said absorbent article is selected from the group consisting of feminine care hygiene articles, baby and child care articles and adult care articles.

\* \* \* \* \*